United States Patent
Higashiyama et al.

(10) Patent No.: US 11,491,290 B2
(45) Date of Patent: Nov. 8, 2022

(54) FLUID CONTROL DEVICE

(71) Applicant: Murata Manufacturing Co., Ltd., Nagaokakyo (JP)

(72) Inventors: Yuzo Higashiyama, Nagaokakyo (JP); Hiroaki Wada, Nagaokakyo (JP)

(73) Assignee: MURATA MANUFACTURING CO., LTD., Kyoto (JP)

(*) Notice: Subject to any disclaimer, the term of this patent is extended or adjusted under 35 U.S.C. 154(b) by 580 days.

(21) Appl. No.: 16/433,073

(22) Filed: Jun. 6, 2019

(65) Prior Publication Data

US 2019/0282771 A1 Sep. 19, 2019

Related U.S. Application Data

(63) Continuation of application No. PCT/JP2017/044221, filed on Dec. 8, 2017.

(30) Foreign Application Priority Data

Dec. 16, 2016 (JP) .............................. JP2016-244751

(51) Int. Cl.
*A61M 16/00* (2006.01)
*F04D 27/00* (2006.01)

(52) U.S. Cl.
CPC ........ *A61M 16/0003* (2014.02); *A61M 16/00* (2013.01); *A61M 16/022* (2017.08);
(Continued)

(58) Field of Classification Search
CPC ............ A61M 16/003; A61M 16/0069; A61M 16/022; A61M 16/0066; F04D 27/00
See application file for complete search history.

(56) References Cited

U.S. PATENT DOCUMENTS 6,644,311 B1* 11/2003 Truitt ................ A61M 16/0069
128/204.18
2002/0023644 A1 2/2002 Berthon-Jones
(Continued)

FOREIGN PATENT DOCUMENTS

JP 08-121381 A 5/1996
JP 11-190646 A 7/1999
(Continued)

OTHER PUBLICATIONS

Official Communication issued in Japanese Patent Application No. 2018-556640, dated May 19, 2020.
(Continued)

*Primary Examiner* — Margaret M Luarca
(74) *Attorney, Agent, or Firm* — Keating & Bennett, LLP

(57) ABSTRACT

A fluid control device includes a case including an internal space that is partitioned by a partition wall into an air blowing chamber and a control chamber. A dividing wall is disposed inside the air blowing chamber to partition an internal space of the air blowing chamber into a first air blowing chamber and a second air blowing chamber. A fan unit is housed in the second air blowing chamber. A differential pressure sensor senses a differential pressure between a pressure inside the first air blowing chamber and a pressure inside the second air blowing chamber. A controller controls a fan based on the sensed differential pressure.

18 Claims, 5 Drawing Sheets

(52) U.S. Cl.
CPC ....... *F04D 27/00* (2013.01); *A61M 2016/003* (2013.01); *A61M 2016/0027* (2013.01)

(56) References Cited

U.S. PATENT DOCUMENTS

| | | |
|---|---|---|
| 2003/0213491 A1 | 11/2003 | Berthon-Jones et al. |
| 2006/0249150 A1 | 11/2006 | Dietz et al. |
| 2016/0310691 A1* | 10/2016 | Bath .................. A61M 16/024 |
| 2017/0211438 A1 | 7/2017 | Suzuki et al. |

FOREIGN PATENT DOCUMENTS

| | | |
|---|---|---|
| JP | 11-325525 A | 11/1999 |
| JP | 2001-037880 A | 2/2001 |
| JP | 2013-252434 A | 12/2013 |
| JP | 2016-034411 A | 3/2016 |
| JP | 2016-123556 A | 7/2016 |

OTHER PUBLICATIONS

Official Communication issued in International Patent Application No. PCT/JP2017/044221, dated Mar. 13, 2018.

* cited by examiner

FLUID CONTROL DEVICE

CROSS REFERENCE TO RELATED APPLICATIONS

This application claims the benefit of priority to Japanese Patent Application No. 2016-244751 filed on Dec. 16, 2016 and is a Continuation Application of PCT Application No. PCT/JP2017/044221 filed on Dec. 8, 2017. The entire contents of each of these applications are hereby incorporated herein by reference.

BACKGROUND OF THE INVENTION

1. Field of the Invention

The present invention relates to a fluid control device used for continuous positive airway pressure (CPAP), for example.

2. Description of the Related Art

Conventionally, for the treatment of sleep-related disorders, such as obstructive sleep apnea (OSA), for example, a fluid control device, such as a continuous positive airway pressure (CPAP) device (which will be hereinafter referred to as a CPAP device) has been used (for example, see Japanese Patent Laid Open No. 2016-34411). The CPAP device includes a device body incorporating a fan, and is configured to supply gas (for example, air) with a pressure higher than an atmospheric pressure from the device body to a mask attached to a mouth or a nose of a patient.

The CPAP device measures the flow rate of gas, for example, by a flow rate sensor provided in a supply path of gas supplied by a fan, and supplies gas with a prescribed pressure. The flow rate sensor provided in an exhaust port includes a straightening vane. The CPAP device obtains the flow rate in the supply path based on the pressure before and after the straightening vane in the supply path.

The CPAP device is used while a patient is sleeping. Thus, when the patient stays out overnight for a business trip, personal travel and the like, the patient needs to carry the CPAP device. The above-described CPAP device includes an exhaust port provided with a flow rate sensor that needs to be provided with a straightening vane, which leads to a pressure loss. Consequently, a larger-sized fan is required, with the result that the CPAP device is increased in size. Therefore, size reduction of the CPAP device (fluid control device) is desired.

SUMMARY OF THE INVENTION

Preferred embodiments of the present invention provide fluid control devices that are each able to be reduced in size.

A fluid control device according to a preferred embodiment of the present invention includes a suction port and an exhaust port, and is configured to rotationally drive a fan to suction a fluid through the suction port from outside and discharge the fluid through the exhaust port. The fluid control device includes a fan unit including the fan and a fan case in which the fan is housed; a controller configured to control driving of the fan; a case including a first air blowing chamber that is in communication with outside through the suction port, a second air blowing chamber in which the fan unit is housed, and a communication portion through which the first air blowing chamber and the second air blowing chamber are in communication with each other; and a differential pressure sensor configured to sense a differential pressure between a pressure inside the first air blowing chamber and a pressure inside the second air blowing chamber.

According to the configuration as described above, the fluid suctioned from outside through the suction port into the first air blowing chamber by rotational driving of the fan flows from the first air blowing chamber through the communication portion into the second air blowing chamber. The communication portion causes a pressure loss in the flow of the fluid, so that a differential pressure occurs between the pressure in the first air blowing chamber and the pressure in the second air blowing chamber. This differential pressure corresponds to the flow rate of the fluid flowing from the first air blowing chamber into the second air blowing chamber, that is, the flow rate of the fluid discharged from the fluid control device. The controller is able to control driving of the fan based on the differential pressure sensed by the differential pressure sensor. Thus, a flow rate sensor does not need to be provided on the inside or the outside of the exhaust port. Accordingly, the fluid control device is able to be reduced in size and weight.

Furthermore, by driving the fan housed in the second air blowing chamber, the fluid flows from outside the device through the suction port, the first air blowing chamber, and the communication portion into the second air blowing chamber. Accordingly, the flow of the fluid is stable in the first air blowing chamber and the second air blowing chamber, so that the pressure inside each of the air blowing chambers is able to be detected with stability.

It is preferable that the differential pressure sensor is configured to sense the differential pressure between the pressure inside the first air blowing chamber and the pressure inside the second air blowing chamber. The pressure inside the first air blowing chamber is obtained by a first pressure sensing portion to sense the pressure inside the first air blowing chamber. The pressure inside the second air blowing chamber is obtained by a second pressure sensing portion to sense the pressure inside the second air blowing chamber.

According to the configuration as described above, an extremely small differential pressure between the pressure inside the first air blowing chamber and the pressure inside the second air blowing chamber is able to be sensed by using the differential pressure sensor. Accordingly, even if the pressure loss between the first air blowing chamber and the second air blowing chamber is small, the differential pressure therebetween is able to be detected, and the fan unit is able to be reduced in size.

In the above-described fluid control device, it is preferable that the controller is configured to control a rotation speed of the fan to be increased when the differential pressure is positive relative to a prescribed value, and to control the rotation speed of the fan to be decreased when the differential pressure is negative relative to the prescribed value.

According to the configuration as described above, the rotation speed of the fan is able to be controlled by simple processing or computation of comparing the differential pressure with a prescribed value, which is advantageous to reduce the computation load in a controller and/or to simplify the structure of the controller.

In the above-described fluid control device, it is preferable that the controller is configured to determine that a respiration state of a patient connected to the exhaust port is an inhalation state when the differential pressure is positive relative to a prescribed value, and to determine that the respiration state of the patient connected to the exhaust port is an exhalation state when the differential pressure is negative relative to the prescribed value.

According to the configuration as described above, the rotation speed of the fan is able to be controlled by simple processing or computation of comparing the differential pressure with a prescribed value, which is advantageous to reduce the computation load in a controller and/or to simplify the structure of the controller.

In the above-described fluid control device, it is preferable that the case includes a control chamber in which the controller is housed, the control chamber being located adjacent to the first air blowing chamber and the second air blowing chamber; the first pressure sensing portion is a first pressure sensing hole provided in a dividing wall between the first air blowing chamber and the control chamber, the first pressure sensing hole being opened toward the first air blowing chamber; and the second pressure sensing portion is a second pressure sensing hole provided in a dividing wall between the second air blowing chamber and the control chamber, the second pressure sensing hole being opened toward the second air blowing chamber.

According to the configuration as described above, the controller is housed in the control chamber that is adjacent to the first air blowing chamber and the second air blowing chamber, which enables a relatively short path through which the pressure in the first air blowing chamber and the pressure in the second air blowing chamber are detected. Thus, the fluid control device is able to be reduced in size.

In the above-described fluid control device, it is preferable that the first pressure sensing hole is opened in a direction orthogonal or substantially orthogonal to a direction in which the suction port is opened, and the second pressure sensing hole is opened in a direction orthogonal or substantially orthogonal to a direction in which the communication portion is opened.

According to the configuration as described above, the first pressure sensing hole is opened in the direction orthogonal or substantially orthogonal to the flow of the fluid that is suctioned through the suction port into the first air blowing chamber, so that the pressure in the first air blowing chamber is able to be sensed without being influenced by the flow of the fluid. Also, the second pressure sensing hole is opened in the direction orthogonal or substantially orthogonal to the flow of the fluid that flows from the communication portion into the second air blowing chamber, so that the pressure in the second air blowing chamber is able to be sensed without being influenced by the flow of the fluid.

In the above-described fluid control device, it is preferable that the controller is configured to convert the differential pressure into a flow rate of the fluid and control the fan based on the flow rate.

According to the configuration as described above, the pressure of the fluid to be supplied is able to be controlled in accordance with the differential pressure.

In the above-described fluid control device, it is preferable that the controller is configured to estimate an exhalation timing based on the flow rate and control the fan in accordance with the exhalation timing to change a pressure of the fluid.

According to the configuration as described above, by estimating the exhalation timing based on the flow rate, the pressure is able to be controlled in accordance with the respiration state of the patient to which the fluid is supplied.

The fluid control devices according to preferred embodiments of the present invention are each able to be reduced in size.

The above and other elements, features, steps, characteristics and advantages of the present invention will become more apparent from the following detailed description of the preferred embodiments with reference to the attached drawings.

DETAILED DESCRIPTION OF THE PREFERRED EMBODIMENTS

In the following, preferred embodiments of the present invention will be described with reference to the accompanying drawings.

In the accompanying drawings, some components may be shown in an enlarged manner to facilitate ease of understanding. The size ratios of some of the components may be different from those of the actual components or those of the corresponding components in another figure. Also, to facilitate ease of understanding, some of the components may not be hatched in cross-sectional views.

Figure 2:
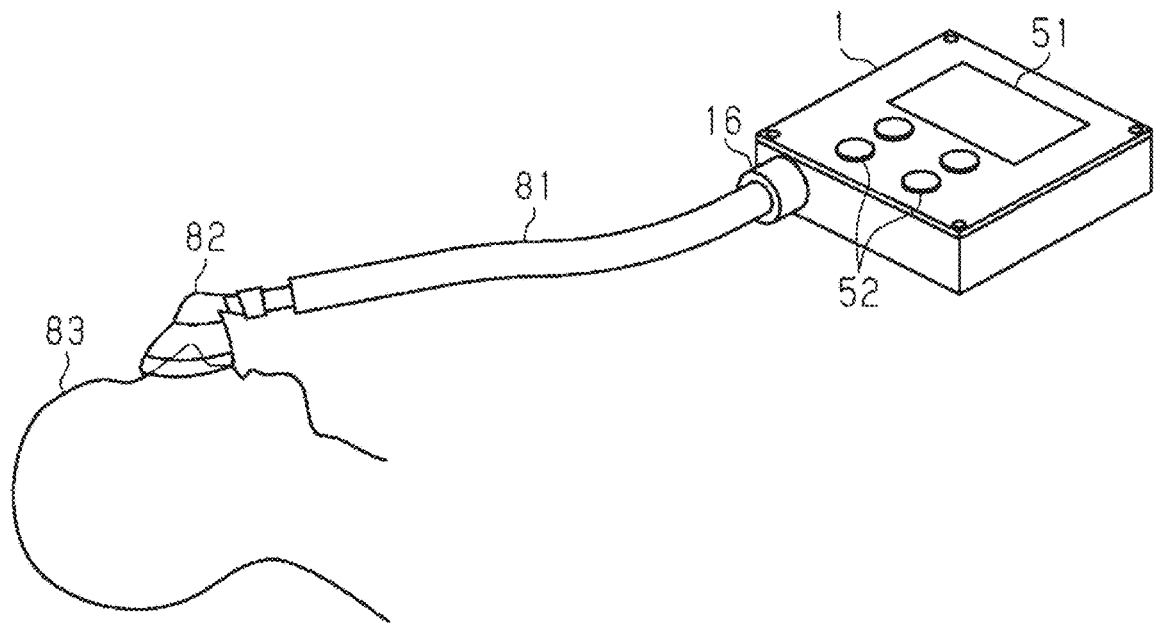
FIG. 2 is a schematic diagram showing the state of use of the fluid control device.

As shown in FIG. 2, a fluid control device 1 according to a preferred embodiment of the present invention is used, for example, as a continuous positive airway pressure (CPAP) device. The fluid control device 1 is connected to a mask 82 through a tube 81. Mask 82 is attached to a mouth or nose of a patient 83. Fluid control device 1 supplies gas (for example, air) with a desired pressure to the patient 83 through the tube 81 and the mask 82. Furthermore, fluid control device 1 determines the state of patient 83 (for example, during exhalation) and controls the pressure of gas to be supplied to patient 83 in accordance with the state of the patient.

Fluid control device 1 includes a case 10, and a display 51 and an operation unit 52 that are disposed on the upper surface of case 10. Fluid control device 1 causes display 51 to display various types of information including setting values. Furthermore, fluid control device 1 sets various types of information including setting values based on the operation on operation unit 52. The setting values include a pressure value of the gas to be supplied and a flow rate value of the gas. Also, the setting values include a pressure value of the gas to be supplied during exhalation.

Fluid control device 1 estimates the exhalation state of patient 83 to which mask 82 is attached. Then, fluid control device 1 controls the pressure value of the gas, which is to be supplied, so as to be synchronized with the estimated exhalation state. For example, the pressure during inhalation is about 1000 Pa while the pressure during exhalation is about 700 Pa. When patient 83 is in the exhalation state, the pressure of the gas to be supplied is lowered, thus reducing the difficulty of breathing of patient 83.

Figure 1A:
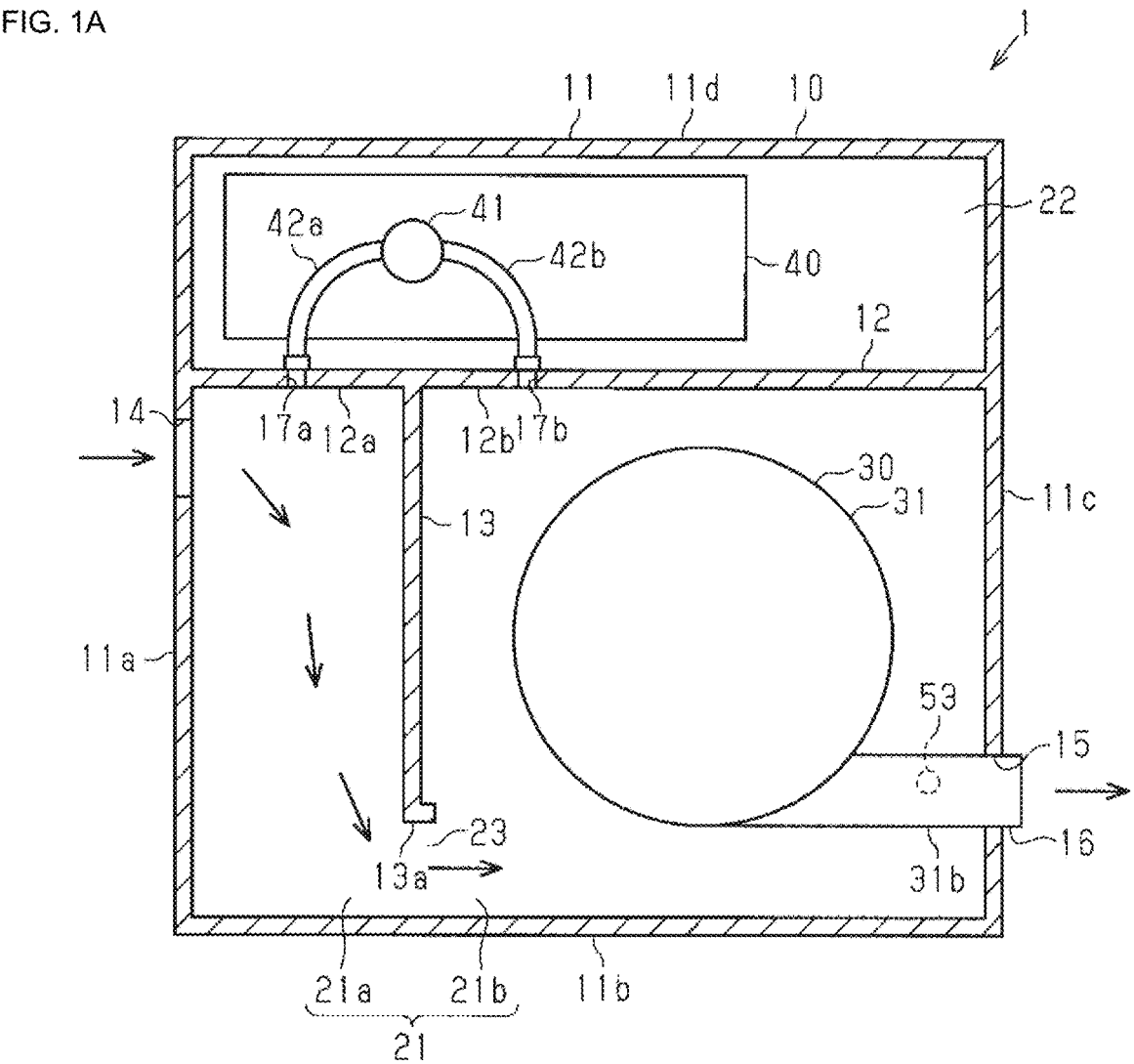
FIG. 1A is a top cross-sectional view schematically showing a fluid control device according to a preferred embodiment of the present invention.
Figure 1B:
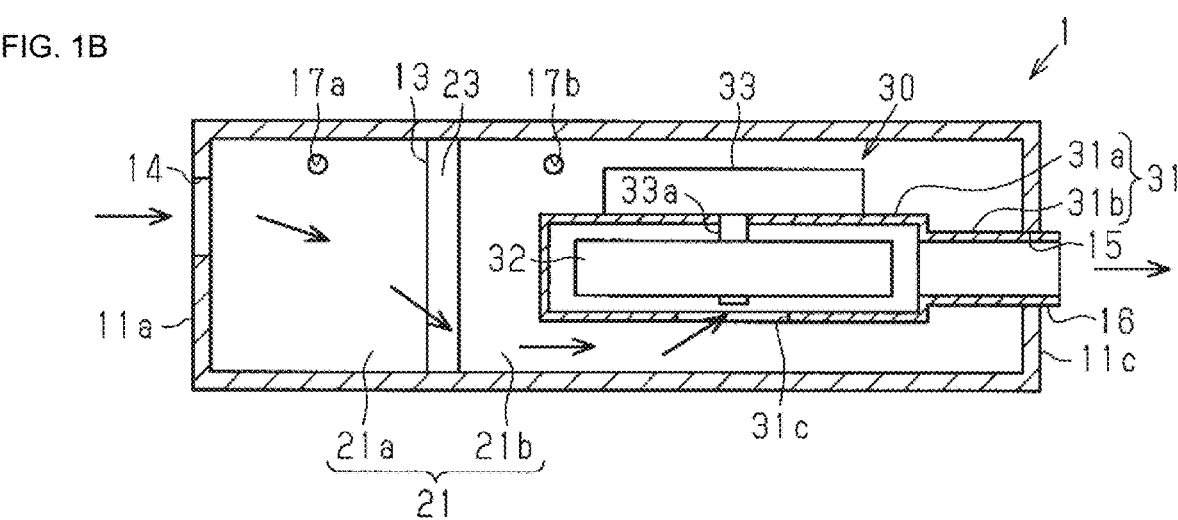
FIG. 1B is a side cross-sectional view schematically showing the fluid control device.

As shown in FIGS. 1A and 1B, fluid control device 1 includes case 10, and a fan unit 30 and a controller 40 that are disposed inside case 10.

Case 10 includes an outer wall 11 and a partition wall 12 that is disposed inside outer wall 11. The internal space of case 10 is partitioned into an air blowing chamber 21 and a control chamber 22 by partition wall 12 that is vertically disposed. In the present preferred embodiment, case 10 preferably has a flat rectangular or substantially rectangular parallelepiped shape, for example. Outer wall 11 includes four outer walls 11a to 11d.

A dividing wall 13 is disposed inside air blowing chamber 21. Dividing wall 13 partitions the internal space of air blowing chamber 21 into a first air blowing chamber 21a and a second air blowing chamber 21b. Dividing wall 13 is connected to partition wall 12 and extends from partition wall 12 toward outer wall 11. Thus, first air blowing chamber 21a and second air blowing chamber 21b are located adjacent to control chamber 22. Dividing wall 13 includes a tip end 13a that is spaced apart from outer wall 11b. By dividing wall 13 and outer wall 11b, a communication portion 23 enabling communication between first air blowing chamber 21a and second air blowing chamber 21b is provided.

As shown in FIG. 1A, outer wall 11a of case 10 is provided with a suction port 14 enabling communication between the inside of case 10 and the outside of case 10. A portion of outer wall 11a provided with suction port 14 defines first air blowing chamber 21a. Thus, suction port 14 enables communication between the inside of first air blowing chamber 21a and the outside of case 10. The suction port 14 is directed in the direction orthogonal or substantially orthogonal to the surface of outer wall 11a (the outside surface and the inside surface of case 10). The direction in which this suction port 14 faces is defined as an opening direction.

Communication portion 23 is provided between tip end 13a of dividing wall 13 and outer wall 11. In other words, communication portion 23 is opened in the thickness direction of dividing wall 13. In the present preferred embodiment, the opening direction of suction port 14 corresponds to the opening direction of communication portion 23. Also, in a view seen in the opening direction, the suction port and communication portion 23 do not overlap with each other.

Fan unit 30 is housed in second air blowing chamber 21b. As shown in FIG. 1B, fan unit 30 includes a fan case 31, a fan 32 housed in fan case 31, and a motor 33 defining and functioning as a driving source for driving fan 32.

Fan case 31 includes a housing portion 31a in which fan 32 is housed, and a discharge portion 31b protruding from the side surface of housing portion 31a. Housing portion 31a is provided with a flow inlet 31c that is opened downward. In case 10, an outer wall 11c defining second air blowing chamber 21b is provided with an insertion port 15 into which discharge portion 31b of fan case 31 is inserted. The end of discharge portion 31b inserted into insertion port 15 protrudes from case 10. This protruding end of discharge portion 31b defines and functions as an exhaust port 16 of the fluid control device 1. Tube 81 shown in FIG. 2 is coupled to the exhaust port 16.

Motor 33 is attached to the upper surface of fan case 31. A rotation shaft 33a of motor 33 is inserted into fan case 31. Fan 32 is attached to rotation shaft 33a of motor 33. Fan 32 is preferably a centrifugal fan, for example.

When fan 32 is rotationally driven by motor 33, gas is fed from suction port 14 through first air blowing chamber 21a into second air blowing chamber 21b as indicated by an arrow shown in FIG. 1A. Then, the gas is suctioned from the inside of second air blowing chamber 21b through flow inlet 31c into fan case 31 as indicated by an arrow shown in FIG. 1B. Then, the gas inside fan case 31 is discharged through discharge portion 31b. The discharged gas is fed to patient 83 through tube 81 and mask 82 that are shown in FIG. 2.

Controller 40 is disposed in control chamber 22. Controller 40 includes a circuit substrate and a plurality of electronic components mounted on the circuit substrate, for example.

A differential pressure sensor 41 is disposed in controller 40. Differential pressure sensor 41 detects the difference (the differential pressure) between the pressure in first air blowing chamber 21a and the pressure in second air blowing chamber 21b.

As shown in FIG. 1A, partition wall 12a between first air blowing chamber 21a and control chamber 22 is provided with a first pressure sensing hole 17a. First pressure sensing hole 17a penetrates through partition wall 12a in a thickness direction thereof. Also, in the present preferred embodiment, first pressure sensing hole 17a is opened in the direction orthogonal or substantially orthogonal to the opening direction of suction port 14 (the direction in which suction port 14 penetrates through outer wall 11a). Furthermore, the opening direction of first pressure sensing hole 17a corresponds to the direction orthogonal or substantially orthogonal to the opening direction of communication portion 23.

First pressure sensing hole 17a is connected to differential pressure sensor 41 through a detection tube 42a. Through the first pressure sensing hole 17a, the pressure in first air blowing chamber 21a is transmitted to differential pressure sensor 41. In other words, first pressure sensing hole 17a defines and functions a pressure sensing portion to detect the pressure in first air blowing chamber 21a.

Similarly, partition wall 12b between second air blowing chamber 21b and control chamber 22 is provided with a second pressure sensing hole 17b. Second pressure sensing hole 17b penetrates through partition wall 12b in the thickness direction thereof. Also, in the present preferred embodiment, second pressure sensing hole 17b is opened in the direction orthogonal or substantially orthogonal to the opening direction of communication portion 23.

Second pressure sensing hole 17b is connected to differential pressure sensor 41 through a detection tube 42b. Through the second pressure sensing hole 17b, the pressure in second air blowing chamber 21b is transmitted to differential pressure sensor 41. In other words, second pressure sensing hole 17b defines and functions as a pressure sensing portion to detect the pressure in second air blowing chamber 21b.

Controller 40 rotationally drives fan 32 based on the detection result obtained by differential pressure sensor 41.

In the following description, the pressure in first air blowing chamber 21a and the pressure in second air blowing chamber 21b may be represented by reference characters P21a and P21b, respectively. The difference between the pressure in first air blowing chamber 21a and the pressure in second air blowing chamber 21b (that is, P21a-P21b) may be represented by a reference character PD. The pressure in first air blowing chamber 21a and the pressure in second air blowing chamber 21b change in accordance with the respiration state of patient 83. Thus, according to one preferred embodiment of the present invention, controller 40 may be configured to compare the pressure in first air blowing chamber 21a and the pressure in second air blowing chamber 21b, to estimate that patient 83 is in the state of inhalation timing when the pressure in first air blowing chamber 21a is higher than the pressure in second air blowing chamber 21b (that is, P21a>P21b), and to estimate that patient 83 is in the state of exhalation timing when the pressure in first air blowing chamber 21a is lower than the pressure in second air blowing chamber 21b (that is, P21a<P21b). When the pressure in first air blowing chamber 21a is the same as the pressure in second air blowing chamber 21b (P21a=P21b), controller 40 may estimate that patient 83 is in the transition period between the exhalation timing and the inhalation timing.

The difference between the pressure in first air blowing chamber 21a and the pressure in second air blowing chamber 21b (P21a-P21b, that is, PD) changes in accordance with the respiration state of patient 83. Thus, according to another preferred embodiment of the present invention, controller 40 may be configured to compare the pressure in first air blowing chamber 21a and the pressure in second air blowing chamber 21b, to estimate that patient 83 is in the state of inhalation timing when difference PD between the pressure in first air blowing chamber 21a and the pressure in second air blowing chamber 21b is higher than a prescribed value Pth (which may be referred to as the first reference value or a respiration state determination value), and to estimate that patient 83 is in the state of exhalation timing when difference PD between the pressure in first air blowing chamber 21a and the pressure in second air blowing chamber 21b is lower than prescribed value Pth. When difference PD is the same as prescribed value Pth, controller 40 may estimate that patient 83 is in the transition period between the exhalation timing and the inhalation timing. This prescribed value Pth is any value that may be zero. Controller 40 may preferably be configured to be capable of setting prescribed value Pth. Although prescribed value Pth may be set in advance as a default value in controller 40, prescribed value Pth may be changed, for example, in accordance with patient 83 or in accordance with the volume of the gas path extending from fluid control device 1 to patient 83. In a specific example in which prescribed value Pth is set at zero, when the pressure in first air blowing chamber 21a is higher than the pressure in second air blowing chamber 21b (that is, P21a>P21b), difference PD between the pressure in first air blowing chamber 21a and the pressure in second air blowing chamber 21b is a positive value, with the result that controller 40 estimates that patient 83 is in the state of inhalation timing. In contrast, when the pressure in first air blowing chamber 21a is lower than the pressure in second air blowing chamber 21b (that is, P21a<P21b), difference PD between the pressure in first air blowing chamber 21a and the pressure in second air blowing chamber 21b is a negative value, with the result that controller 40 estimates that patient 83 is in the state of exhalation timing.

In some examples, controller 40 may preferably be configured to determine whether to increase or decrease the rotation speed of fan 32 in accordance with the value of difference PD between the pressure in first air blowing chamber 21a and the pressure in second air blowing chamber 21b. Specifically, controller 40 may be configured to compare the pressure in first air blowing chamber 21a and the pressure in second air blowing chamber 21b, to perform control to increase the rotation speed of fan 32 when the pressure in first air blowing chamber 21a is higher than the pressure in second air blowing chamber 21b (that is, PD is a positive value), and to perform control to decrease the rotation speed of fan 32 when the pressure in first air blowing chamber 21a is lower than the pressure in second air blowing chamber 21b (that is, PD is a negative value). For example, controller 40 is preferably configured to increase the rotation speed of fan 32 gradually or in a stepwise manner as the pressure in first air blowing chamber 21a becomes higher than the pressure in second air blowing chamber 21b (that is, as PD becomes greater), and to decrease the rotation speed of fan 32 gradually or in a stepwise manner as the pressure in first air blowing chamber 21a becomes lower than the pressure in second air blowing chamber 21b (that is, as PD becomes smaller).

In some examples, controller 40 may preferably be configured to compare the pressure in first air blowing chamber 21a and the pressure in second air blowing chamber 21b over time, thus checking the respiration state of the patient. For example, controller 40 may be configured to determine that the state of the patient has changed from the inhalation state to the exhalation state based on the event that the state in which the pressure in first air blowing chamber 21a is higher than the pressure in second air blowing chamber 21b (that is, PD is a positive value) has changed to the state in which the pressure in first air blowing chamber 21a is the same as or lower than the pressure in second air blowing chamber 21b (that is, PD is a negative value or zero). In contrast, controller 40 may preferably be configured to determine that the state of patient 83 has changed from the exhalation state to the inhalation state based on the event that the state in which the pressure in first air blowing chamber 21a is lower than the pressure in second air blowing chamber 21b (that is, PD is a negative value) has changed to the state in which the pressure in first air blowing chamber 21a is the same as or higher than the pressure in second air blowing chamber 21b (that is, PD is a positive value or zero).

Furthermore, the respiration state of patient 83 is able to be checked by comparing the changes in differential pressures between the pressures in first air blowing chamber 21a and the pressures in second air blowing chamber 21b at a plurality of points. For example, controller 40 may be configured to determine whether patient 83 is in the inhalation state or in the exhalation state, based on the changing trend (an increasing trend or a decreasing trend) of difference PD between the pressure in first air blowing chamber 21a and the pressure in second air blowing chamber 21b that are sensed at a plurality of points at intervals.

Furthermore, in some examples, controller 40 may preferably be configured to determine that air leakage from mask or the like occurs when an average value MP21 of the differential pressure between the pressure in first air blowing chamber 21a and the pressure in second air blowing chamber 21b is greater than a prescribed value Mth (which may be referred to as the second reference value or a leakage determination value). For example, controller 40 may preferably be configured to monitor the differential pressure between the pressure in first air blowing chamber 21a and the pressure in second air blowing chamber 21b, calculate average value MP21 of the differential pressure between the pressure in first air blowing chamber 21a and the pressure in second air blowing chamber 21b at the controlled timing or periodically, compare the calculated average value MP21 of the differential pressure with leakage determination value Mth, and, when average value MP21 is greater than leakage determination value Mth, determine that air leakage occurs. Controller 40 may preferably be configured, for example, to cause display 51 to display occurrence of air leakage when it determines that air leakage occurs.

The following is an explanation about a specific example of controller 40 according to a preferred embodiment of the present invention configured to estimate the flow rate of gas based on the differential pressure or to convert the differential pressure into a flow rate of gas. For example, controller 40 obtains the flow rate of gas based on the detection result obtained by differential pressure sensor 41. In fluid control device 1, gas flows from the outside of case 10 through the gas path of suction port 14, first air blowing chamber 21a, communication portion 23, second air blowing chamber 21b, and fan unit 30 and then is discharged through exhaust port 16. Then, the gas is supplied from exhaust port 16 through tube 81 and mask 82 to patient 83 as shown in FIG. 2.

In the above-described gas path, a pressure loss occurs in communication portion 23. This causes a difference between the pressure in first air blowing chamber 21a and the pressure in second air blowing chamber 21b. This differential pressure changes in accordance with the flow rate of gas. Controller 40 measures the differential pressure between first air blowing chamber 21a and second air blowing chamber 21b using differential pressure sensor 41 to obtain the flow rate of the gas. For example, controller 40 calculates the flow rate based on an arithmetic expression. An example of arithmetic expressions may be represented as $FR = K1 \times PD^{K2}$, where the flow rate (m/s) is defined as FR, the differential pressure (Pa) is defined as PD, and coefficients are defined as K1 and K2. Coefficients K1 and K2 are calculated in advance, for example, by experimentation, simulation, and other suitable methods. Preferably, coefficient K1 is, for example, 10 and coefficient K2 is, for example, 0.5. In addition, a table including the flow rate and the differential pressure associated with each other may be stored in advance, and the differential pressure may be converted into a flow rate by reference to the stored table.

Figure 3:
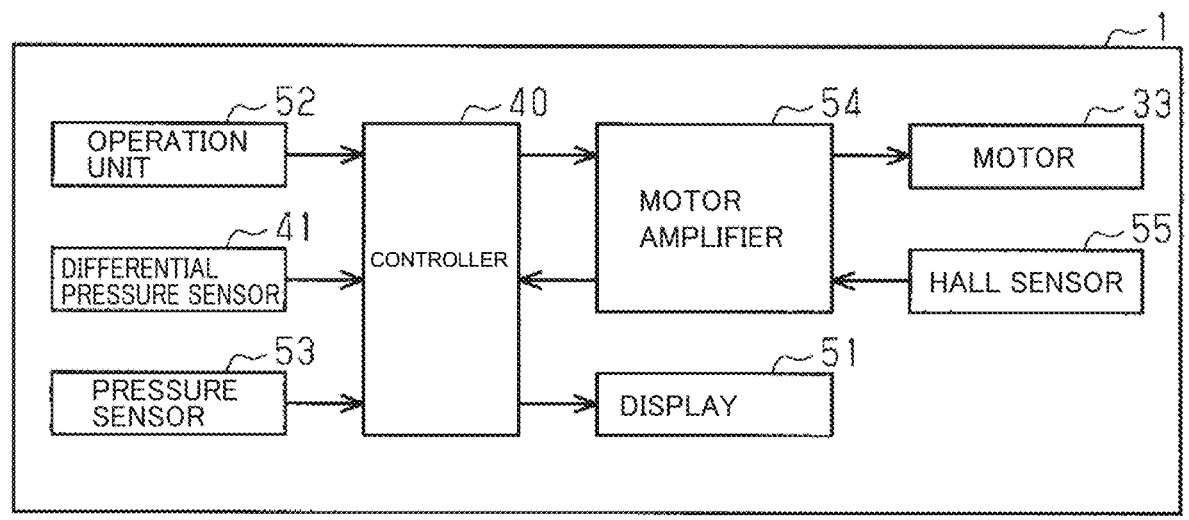
FIG. 3 is a block diagram showing the electrical configuration of the fluid control device.

FIG. 3 shows the electrical configuration of fluid control device 1.

As shown in FIG. 3, fluid control device 1 includes display 51, operation unit 52, motor 33, controller 40, a pressure sensor 53, differential pressure sensor 41, a motor amplifier 54, and a Hall sensor 55.

Pressure sensor 53 is provided in fan case 31, for example, as shown in FIG. 1A and configured to detect the pressure of the gas discharged from fan unit 30.

Differential pressure sensor 41 is provided in controller 40 shown in FIG. 1A.

Controller 40 outputs a drive command (speed command) to motor amplifier 54. Motor amplifier 54 supplies the driving current according to the drive command to motor 33. Motor 33 rotates according to the supplied driving current. In other words, motor 33 rotates at the rotation speed according to the drive command.

Hall sensor 55 is provided in motor 33 and outputs a signal according to rotation of motor 33. Motor amplifier 54 converts the output signal from Hall sensor 55 into a voltage. Controller 40 obtains the rotation speed of motor 33 based on the voltage output from motor amplifier 54. Then, controller 40 controls the rotation speed of motor 33 to discharge gas at a desired pressure.

Controller 40 stores various types of setting values. The setting values preferably include, for example, a reference pressure value, a decompression amount, and a flow rate determination value.

Controller 40 determines the rotation speed of motor 33 based on the actual pressure value detected by pressure sensor 53 and the reference pressure command included in the setting values. By rotation of motor 33, the gas is discharged from fluid control device 1. Controller 40 calculates the pressure command value based on the reference pressure command and the decompression amount. Based on the difference between the pressure command value and the actual pressure value, controller 40 controls the pressure of the gas discharged from fluid control device 1.

Controller 40 estimates the exhalation timing of patient 83 based on the flow rate obtained by differential pressure sensor 41. For example, the flow rate of the gas in fluid control device 1 changes in accordance with the respiration state of patient 83. Based on the flow rate, controller 40 estimates the timing at which inhalation changes to exhalation (the exhalation timing). Then, based on the estimated exhalation timing, controller 40 controls the pressure of the gas that is to be supplied to patient 83.

Controller 40 changes the pressure command value based on the respiration state of patient 83. For example, controller 40 sets the reference pressure command value as a pressure command value when the patient is in the inhalation state. Thus, the gas with a reference pressure is supplied to patient 83. On the other hand, when patient 83 is in the exhalation state, controller 40 sets the value, which is obtained by adding the decompression amount to the reference pressure command value, as a pressure command value. Thus, the pressure of the gas to be supplied to patient 83 is lowered. The reference pressure command value and the decompression amount are set in accordance with patient 83.

Figure 4:
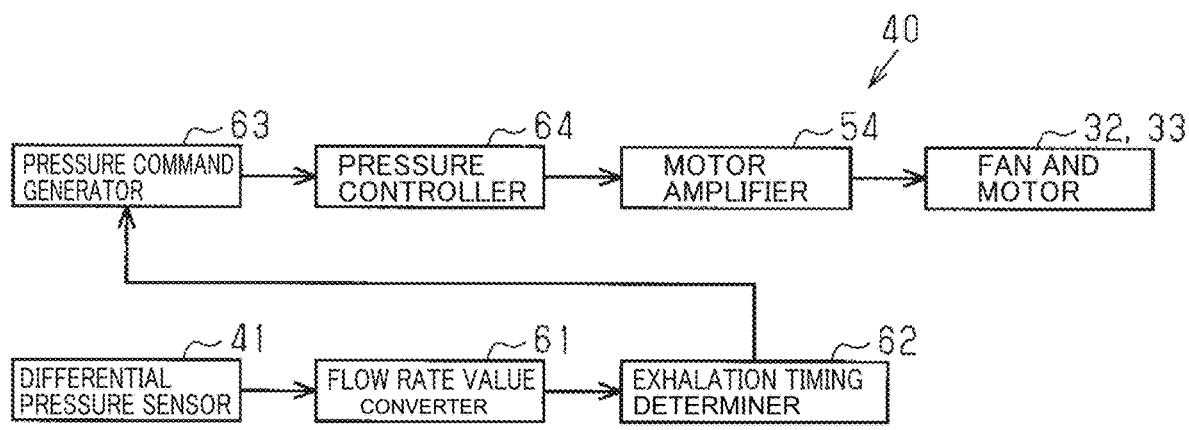
FIG. 4 is a block diagram showing the schematic configuration of a controller according to a preferred embodiment of the present invention.

FIG. 4 is a partial block circuit diagram of controller 40, which shows a control block according to driving of motor 33.

Controller 40 includes a flow rate value converter 61, an exhalation timing determiner 62, a pressure command generator 63, and a pressure controller 64.

Flow rate value converter 1 converts the differential pressure obtained by differential pressure sensor 41 into a flow rate.

Exhalation timing determiner 62 determines the exhalation timing based on the converted flow rate.

Based on the determination result of exhalation timing determiner 62, pressure command generator 63 generates a pressure command value in accordance with the respiration state of patient 83.

According to the pressure command value, pressure controller 64 generates a drive command value used to drive motor 33. Also, based on the detection result of pressure sensor 53, pressure controller 64 controls the drive command value such that the pressure of the gas to be discharged becomes equal to a desired pressure (a pressure command value).

Motor amplifier 54 supplies the current in accordance with the drive command value to motor 33. Motor 33 rotates according to the supplied current.

The advantageous effects of the fluid control device 1 according to the present preferred embodiment will be described below.

Fluid control device 1 includes case 10, and fan unit 30 and controller 40 that are housed in case 10. The internal space of case 10 is partitioned into air blowing chamber 21 and control chamber 22 by partition wall 12 that is vertically arranged. Controller 40 is housed in control chamber 22. Dividing wall 13 is disposed inside air blowing chamber 21. The internal space of air blowing chamber 21 is partitioned into first air blowing chamber 21a and second air blowing chamber 21b. Fan unit 30 is housed in second air blowing chamber 21b.

Partition wall 12a between first air blowing chamber 21a and control chamber 22 is provided with first pressure sensing hole 17a. Partition wall 12b between second air blowing chamber 21b and control chamber 22 is provided with second pressure sensing hole 17b. Controller 40 detects the differential pressure between the pressure inside first air blowing chamber 21a and the pressure inside second air blowing chamber 21b by differential pressure sensor 41, and controls fan 32 based on the differential pressure.

The gas suctioned by rotational driving of fan 32 from outside through suction port 14 into first air blowing chamber 21a flows from first air blowing chamber 21a through communication portion 23 into second air blowing chamber 21b. Communication portion 23 causes a pressure loss in the flow of the gas, so that a differential pressure occurs between the pressure in first air blowing chamber 21a and the pressure in second air blowing chamber 21b. This differential pressure corresponds to the flow rate of the gas that flows from first air blowing chamber 21a into second air blowing chamber 21b, that is, the flow rate of the gas discharged from fluid control device 1. Accordingly, the flow rate of the gas is able to be calculated without a flow rate sensor on the inside or the outside of the exhaust port.

An uneven gas flow occurs on the discharge side with respect to fan unit 30. In contrast, in the present preferred embodiment, by fan 32 housed in second air blowing chamber 21b, gas flows from the outside of the device through suction port 14, first air blowing chamber 21a, and communication portion 23 into second air blowing chamber 21b. Thus, the flow of the gas is stable in first air blowing chamber 21a and second air blowing chamber 21b, so that the pressure inside each of the chambers is able to be detected with stability.

A flow rate sensor according to the related art is disposed in a gas supply path, for example. The flow rate sensor includes a straightening vane and detects the flow rate based on the pressure before and after the straightening vane. The straightening vane causes a pressure loss in the gas. Accordingly, when the flow rate sensor is disposed in a gas supply path, the pressure loss occurs in the flow rate sensor. Thus, in accordance with the pressure loss, the pressure of the gas to be discharged needs to be raised in the fluid control device as a supply source in order to supply gas to a supply destination with a desired pressure. As a result, the fluid control device according to the related art is increased in size.

On the other hand, in fluid control device 1 in the present preferred embodiment, the differential pressure between the pressure in first air blowing chamber 21a and the pressure in second air blowing chamber 21b is detected in the path of the gas between fan unit 30 and suction port 14, that is, on the upstream side of fan unit 30. Since the flow of the gas in first air blowing chamber 21a and second air blowing chamber 21b is stable, a differential pressure is able to be detected even by a small pressure loss. Thus, since a large pressure loss does not need to be caused, a small-sized fan unit 30 is able to be used, so that fluid control device 1 is able to be reduced in size.

The noise generated by rotational driving of fan 32 in fan unit 30 is emitted to the outside through a path of fan unit 30, second air blowing chamber 21b, communication portion 23, first air blowing chamber 21a, and suction port 14. In this path, the noise hits the inner wall of the path, so that the noise is decreased. Thus, the noise emitted from fluid control device 1 to the outside is decreased, so that the quietness of fluid control device 1 is able to be improved.

Controller 40 converts the differential pressure into a flow rate of gas, estimates the exhalation timing based on the flow rate, and controls fan 32 in accordance with the exhalation timing to change the pressure of the gas. In this manner, by converting the differential pressure into a flow rate of gas, and estimating the exhalation timing based on the flow rate, the pressure is able to be controlled in accordance with the respiration state of the patient to which gas is supplied.

Case 10 includes control chamber 22 that is located adjacent to first air blowing chamber 21a and second air blowing chamber 21b, and that houses controller 40. First pressure sensing hole 17a is provided in the dividing wall between first air blowing chamber 21a and the control chamber, and opened toward first air blowing chamber 21a. Second pressure sensing hole 17b is provided in the dividing wall between second air blowing chamber 21b and the control chamber, and opened toward second air blowing chamber 21b. Thus, controller 40 is housed in control chamber 22 that is adjacent to first air blowing chamber 21a and second air blowing chamber 21b, thus enabling a relatively short path through which the pressure in first air blowing chamber 21a and the pressure in second air blowing chamber 21b are detected. Accordingly, fluid control device 1 is able to be reduced in size.

First pressure sensing hole 17a is opened in the direction orthogonal or substantially orthogonal to the opening direction of suction port 14. Second pressure sensing hole 17b is opened in the direction orthogonal or substantially orthogonal to the opening direction of communication portion 23. Thus, first pressure sensing hole 17a is opened in the direction orthogonal or substantially orthogonal to the flow of the gas suctioned from suction port 14 into first air blowing chamber 21a, so that the pressure in first air blowing chamber 21a is able to be sensed without being influenced by the flow of the gas. Also, second pressure sensing hole 17b is opened in the direction orthogonal or substantially orthogonal to the flow of the gas flowing from communication portion 23 into second air blowing chamber 21b, so that the pressure in second air blowing chamber 21b is able to be sensed without being influenced by the flow of the gas.

As described above, the following advantageous effects are achieved according to the present preferred embodiment.

(1) The internal space of case 10 in fluid control device 1 is partitioned by partition wall 12 into air blowing chamber 21 and control chamber 22. A dividing wall 13 is disposed inside air blowing chamber 21 to partition the internal space of air blowing chamber 21 into first air blowing chamber 21a and second air blowing chamber 21b. Fan unit 30 is housed in second air blowing chamber 21b. Partition wall 12a between first air blowing chamber 21a and control chamber 22 is provided with first pressure sensing hole 17a. Partition wall 12b between second air blowing chamber 21b and control chamber 22 is provided with second pressure sensing hole 17b. By differential pressure sensor 41, controller 40 detects the differential pressure between the pressure inside first air blowing chamber 21a and the pressure inside second air blowing chamber 21b. Then, controller 40 controls fan 32 based on the differential pressure.

The gas suctioned by rotational driving of fan 32 from outside through suction port 14 into first air blowing chamber 21a flows from first air blowing chamber 21a through communication portion 23 into second air blowing chamber 21b. Communication portion 23 causes a pressure loss in the flow of the gas, so that a differential pressure occurs between the pressure in first air blowing chamber 21a and the pressure in second air blowing chamber 21b. This differential pressure corresponds to the flow rate of the gas that flows from first air blowing chamber 21a into second air blowing chamber 21b, that is, the flow rate of the gas discharged from fluid control device 1. Accordingly, the flow rate of the gas is able to be obtained without a flow rate sensor on the inside or the outside of the exhaust port. Therefore, fluid control device 1 is able to be reduced in size and weight.

(2) The noise generated by rotational driving of fan 32 in fan unit 30 is emitted to the outside through a path of fan unit 30, second air blowing chamber 21b, communication portion 23, first air blowing chamber 21a, and suction port 14. In this path, the noise hits the inner wall of the path, so that the noise is decreased. Thus, the noise emitted from fluid control device 1 to the outside is decreased, so that the quietness of fluid control device 1 is able to be improved.

(3) Controller 40 converts the differential pressure into a flow rate of gas, estimates the exhalation timing based on the flow rate, and controls fan 32 in accordance with the exhalation timing to change the pressure of the gas. In this manner, by converting the differential pressure into a flow rate of gas, and estimating the exhalation timing based on the flow rate, the pressure is able to be controlled in accordance with the respiration state of the patient to which gas is supplied.

(4) Case 10 includes control chamber 22 that is located adjacent to first air blowing chamber 21a and second air blowing chamber 21b, and that houses controller 40. First pressure sensing hole 17a is provided in the dividing wall between first air blowing chamber 21a and the control chamber, and opened toward first air blowing chamber 21a. Second pressure sensing hole 17b is provided in the dividing wall between second air blowing chamber 21b and the control chamber, and opened toward second air blowing chamber 21b. Thus, controller 40 is housed in control chamber 22 that is adjacent to first air blowing chamber 21a and second air blowing chamber 21b, thus enabling a relatively short path through which the pressure in first air blowing chamber 21a and the pressure in second air blowing chamber 21b are detected. Accordingly, fluid control device 1 is able to be reduced in size.

(5) First pressure sensing hole 17a is opened in the direction orthogonal or substantially orthogonal to the opening direction of suction port 14. Second pressure sensing hole 17b is opened in the direction orthogonal or substantially orthogonal to the opening direction of communication portion 23. Thus, first pressure sensing hole 17a is opened in the direction orthogonal or substantially orthogonal to the flow of the gas suctioned from suction port 14 into first air blowing chamber 21a, so that the pressure in first air blowing chamber 21a is able to be sensed without being influenced by the flow of the gas. Also, second pressure sensing hole 17b is opened in the direction orthogonal or substantially orthogonal to the flow of the gas flowing from communication portion 23 into second air blowing chamber 21b, so that the pressure in second air blowing chamber 21b is able to be sensed without being influenced by the flow of the gas.

Each of the above-described preferred embodiments may be implemented in the following manner.

In the following description, the same or substantially the same components as those in the above-described preferred embodiments will be designated by the same reference characters, and a portion of all of the description thereof will not be repeated. Also, the reference characters of the components not related to the description may be omitted.

The configuration of the fluid control device may be modified as appropriate with respect to the above-described preferred embodiments.

Figure 5:
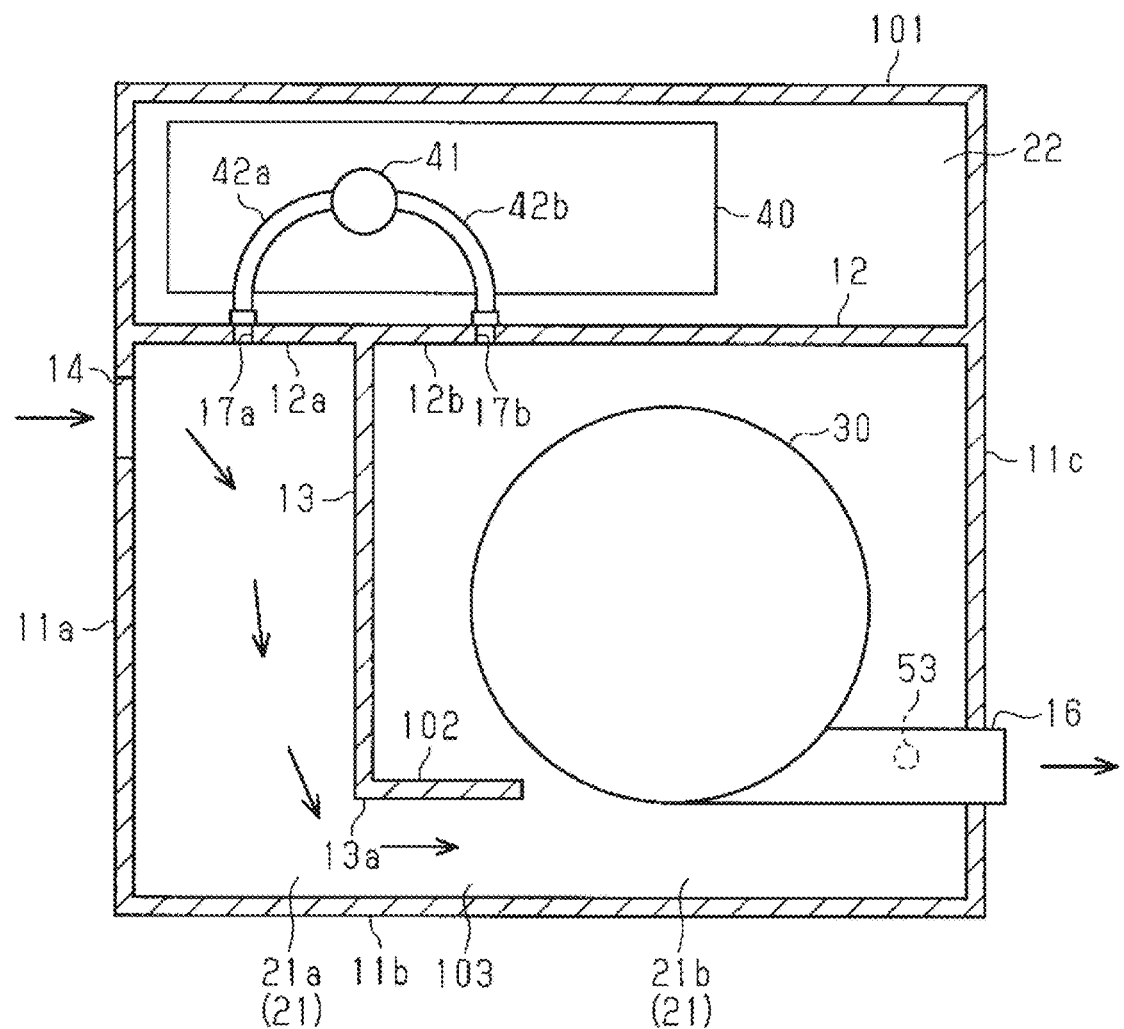
FIG. 5 is a top cross-sectional view schematically showing a fluid control device according to a modification of a preferred embodiment of the present invention.

A fluid control device 101 according to a modification of a preferred embodiment of the present invention shown in FIG. 5 includes a path wall 102 extending from a tip end 13a of a dividing wall 13. A communication portion 103 is provided between the path wall 102 and an outer wall 11b of a case 10. By communication portion 103 extending in this manner, the flow of the gas flowing from first air blowing chamber 21a into second air blowing chamber 21b is stabilized. Accordingly, the pressure in first air blowing chamber 21a and the pressure in second air blowing chamber 21b are able to be detected with stability. Also by communication portion 103 extending as described above, the noise transmitted from second air blowing chamber 21b to first air blowing chamber 21a is decreased, so that the quietness of fluid control device 1 is able to be improved.

Figure 6:
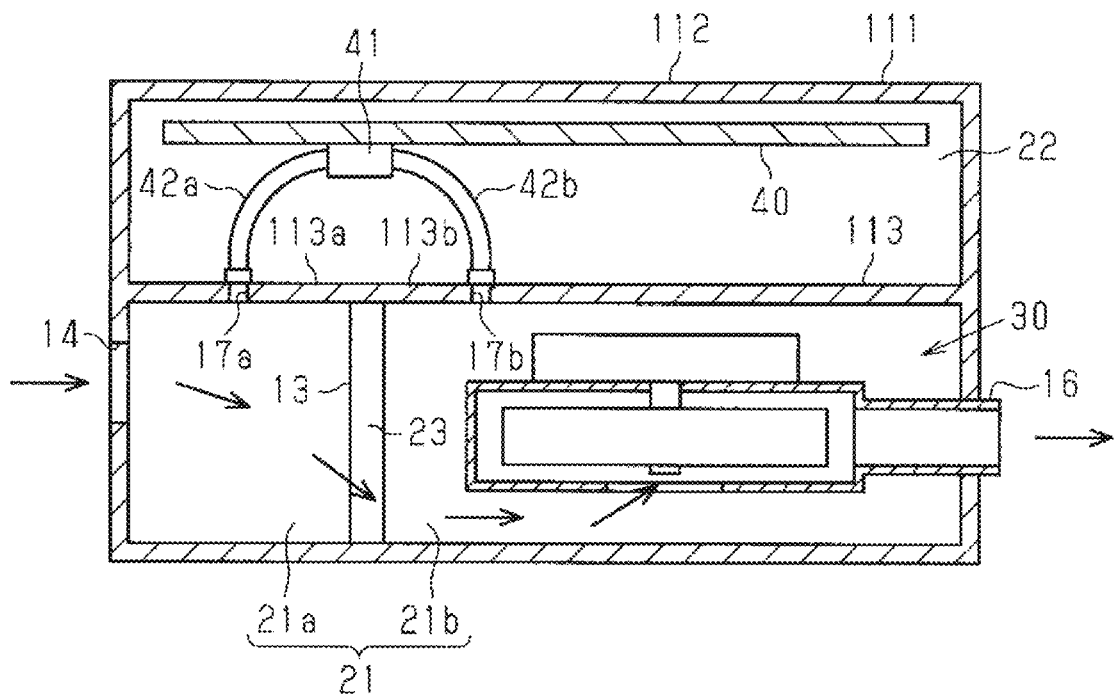
FIG. 6 is a longitudinal cross-sectional view schematically showing a fluid control device according to a modification of a preferred embodiment of the present invention.

A fluid control device 111 according to a modification of a preferred embodiment of the present invention shown in FIG. 6 includes a partition wall 113 partitioning a case 112 in the up-down direction, and also includes an air blowing chamber 21 and a control chamber 22 that are disposed on the lower side and the upper side, respectively, of case 112 due to the existence of partition wall 113. Air blowing chamber 21 is partitioned by dividing wall 13 into first air blowing chamber 21a and second air blowing chamber 21b. Furthermore, a first pressure sensing hole 17a to detect the pressure in first air blowing chamber 21a is provided in a partition wall 113a between first air blowing chamber 21a and control chamber 22, that is, in a ceiling plane of first air blowing chamber 21a. Similarly, a second pressure sensing hole 17b to detect the pressure in second air blowing chamber 21b is provided in a partition wall 113b between second air blowing chamber 21b and control chamber 22, that is, in a ceiling plane of second air blowing chamber 21b. In contrast, first air blowing chamber 21a and second air blowing chamber 21b may be disposed above control chamber 22.

Figure 7:
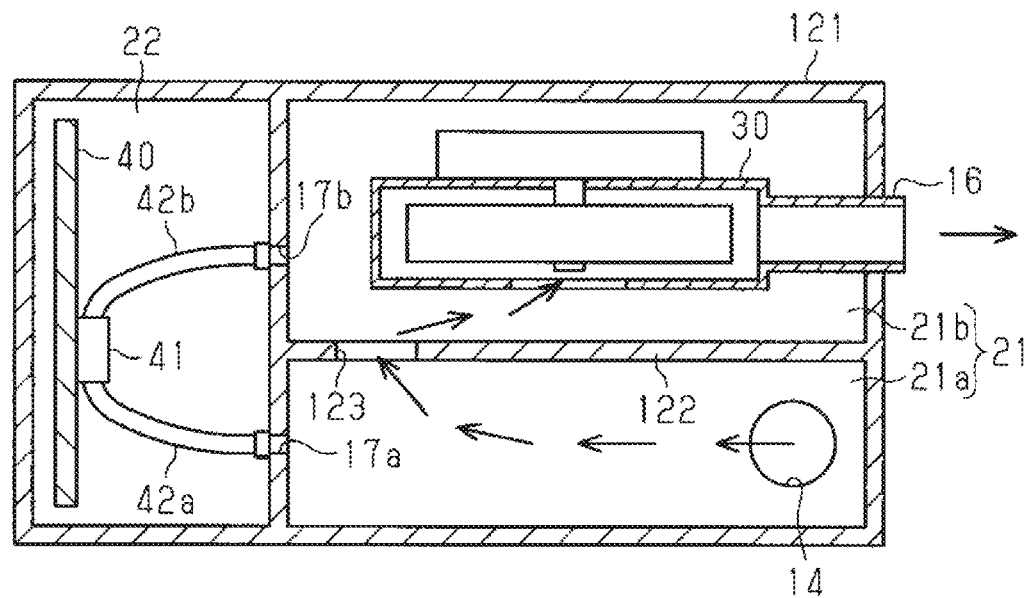
FIG. 7 is a longitudinal cross-sectional view schematically showing a fluid control device according to a modification of a preferred embodiment of the present invention.

A fluid control device 121 according to a modification of a preferred embodiment of the present invention shown in FIG. 7 includes a first air blowing chamber 21a and a second air blowing chamber 21b that is disposed above first air blowing chamber 21a. Also, a control chamber 22 is disposed on the side (on the left side in FIG. 7) of first air blowing chamber 21a and second air blowing chamber 21b. A dividing wall 122 defining and functioning as a partition between first air blowing chamber 21a and second air blowing chamber 21b in the up-down direction is provided with a communication portion 123 enabling communication between first air blowing chamber 21a and second air blowing chamber 21b. In contrast, second air blowing chamber 21b may be disposed below first air blowing chamber 21a.

Figure 8:
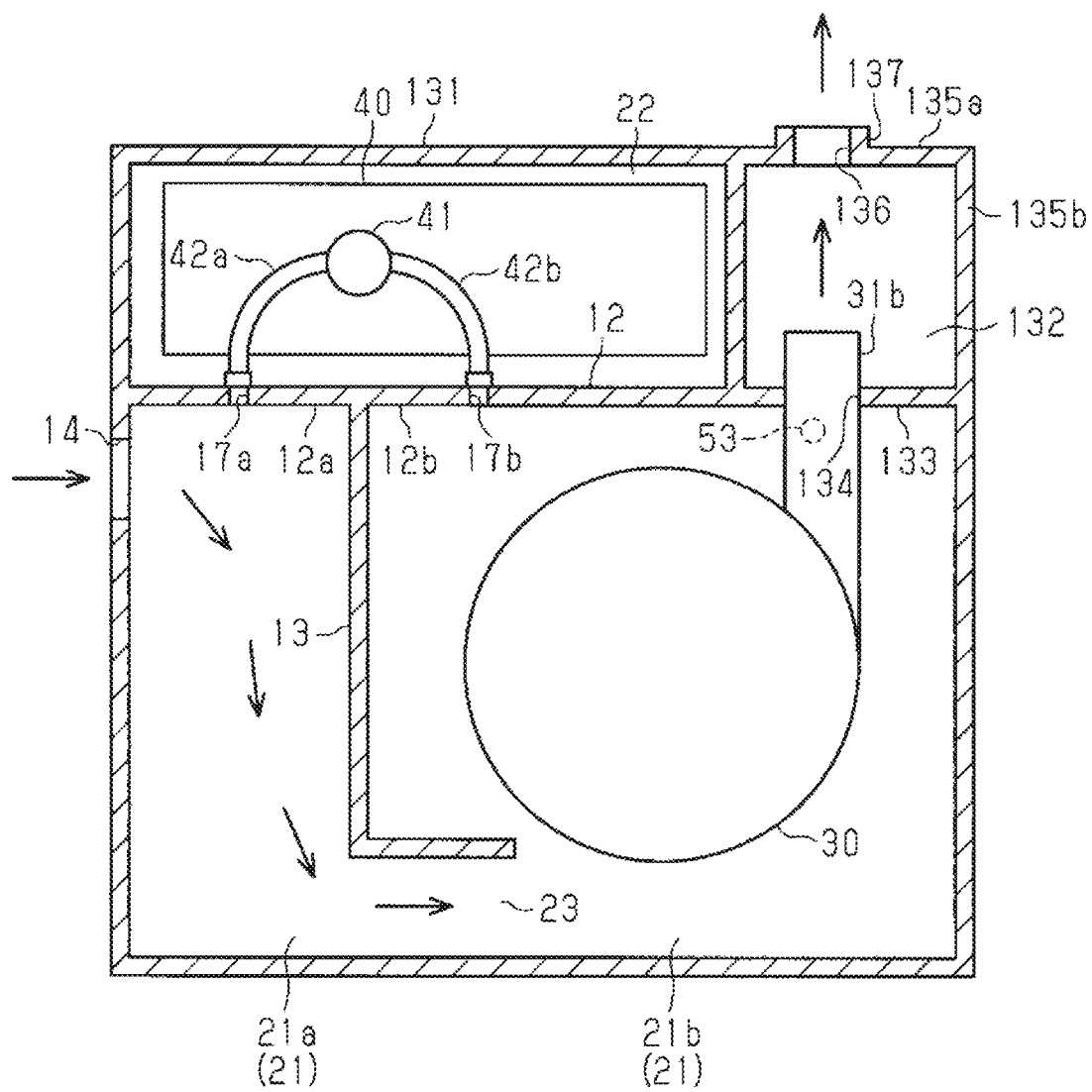
FIG. 8 is a top cross-sectional view schematically showing a fluid control device according to a modification a preferred embodiment of the present invention.

A fluid control device 131 according to a modification of a preferred embodiment of the present invention shown in FIG. 8 includes a third air blowing chamber 132 that is adjacent to a second air blowing chamber 21b. A dividing wall 133 between second air blowing chamber 21b and third air blowing chamber 132 is provided with an insertion hole 134, through which a discharge portion 31b of a fan unit 30 is inserted. An outer wall 135a defining third air blowing chamber 132 is provided with a discharge port 136 penetrating through outer wall 135a, and an exhaust port 137 protruding from outer wall 135*a*. A tube 81 (see FIG. 2) is connected to the exhaust port 137.

In addition, discharge port 136 and exhaust port 137 may be disposed in outer wall 135*b* that define third air blowing chamber 132. Furthermore, a pressure sensor 53 may be disposed in third air blowing chamber 132 to detect the pressure of the gas discharged from fluid control device 131.

In the above-described preferred embodiments, differential pressure sensor 41 is used to detect the differential pressure between the pressure in first air blowing chamber 21*a* and the pressure in second air blowing chamber 21*b*. In contrast, two pressure sensors having the same or substantially the same characteristics may be used to respectively detect the pressure in first air blowing chamber 21*a* and the pressure in second air blowing chamber 21*b*, thus obtaining the differential pressure between the detected pressures.

In the above-described preferred embodiments, first pressure sensing hole 17*a* to detect pressure is provided in partition wall 12*a* between first air blowing chamber 21*a* and control chamber 22 while second pressure sensing hole 17*b* to detect pressure is provided in partition wall 12*b* between second air blowing chamber 21*b* and control chamber 22. However, at least one of the pressure sensing holes may be provided at another position. For example, a pressure sensing hole may be provided in dividing wall 13 between first air blowing chamber 21*a* and second air blowing chamber 21*b* shown in FIGS. 1A and 1B. In this case, one of the detection tubes to connect the pressure sensing hole and the differential pressure sensor may be exposed in first air blowing chamber 21*a* or second air blowing chamber 21*b*. Furthermore, the detection tube may be embedded in dividing wall 13. Furthermore, for example, dividing wall 13 may have a two-layered structure, and the detection tube may be disposed between two dividing walls 13.

The above-described preferred embodiments have been described with reference to the instance in which gas (for example, air) is supplied as a fluid, but may be used additionally when a gas-liquid mixture and the like containing a liquid in mist form is supplied. Also in the above-described preferred embodiments, fluid control device 1 is connected to patient 83 through tube 81 and mask 82, but a cannula may be used in place of mask 82.

The fluid control devices in the above preferred embodiments have been described with reference to an example in which it is used a continuous positive airway pressure device, for example, but may be used for other purposes. Examples of other purposes may be various types of respirators. Examples of various types of respirators may be a bilevel positive airway pressure (BIPAP), a pressure support ventilation (PSV), and the like.

In the above-described preferred embodiments, controller 40 is configured to estimate the flow rate of gas based on the differential pressure or convert the differential pressure into a flow rate of gas, but controller 40 does not necessarily have to calculate or estimate the flow rate of gas based on the differential pressure.

Although no limitation is intended, for example, controller 40 may be configured to control the rotation speed of fan 32 directly based on the differential pressure.

Although no limitation is intended, for example, controller 40 may be configured to compare the pressure in first air blowing chamber 21*a* and the pressure in second air blowing chamber 21*b*, to estimate that patient 83 is in the state of inhalation timing when the pressure in first air blowing chamber 21*a* is higher than the pressure in second air blowing chamber 21*b*, and to estimate that patient 83 is in the state of exhalation timing when the pressure in first air blowing chamber 21*a* is lower than the pressure in second air blowing chamber 21*b*.

Although no limitation is intended, for example, controller 40 may be configured to compare the pressure in first air blowing chamber 21*a* and the pressure in second air blowing chamber 21*b*, to estimate that patient 83 is in the state of inhalation timing when the difference between the pressure in first air blowing chamber 21*a* and the pressure in second air blowing chamber 21*b* is higher than prescribed value Pth, and to estimate that patient 83 is in the state of exhalation timing when the difference between the pressure in first air blowing chamber 21*a* and the pressure in second air blowing chamber 21*b* is lower than prescribed value Pth.

Although no limitation is intended, for example, controller 40 may be configured to determine whether to increase or decrease the rotation speed of fan 32 based on the value of the differential pressure between the pressure in first air blowing chamber 21*a* and the pressure in second air blowing chamber 21*b*. For example, controller 40 may be configured to compare the pressure in first air blowing chamber 21*a* and the pressure in second air blowing chamber 21*b*, to perform control to increase the rotation speed of fan 32 when the pressure in first air blowing chamber 21*a* is higher than the pressure in second air blowing chamber 21*b*, and to perform control to decrease the rotation speed of fan 32 when the pressure in first air blowing chamber 21*a* is lower than the pressure in second air blowing chamber 21*b*.

Although no limitation is intended, for example, controller 40 may be configured to compare the pressure in first air blowing chamber 21*a* and the pressure in second air blowing chamber 21*b* over time to thus check the respiration state of the patient.

Although no limitation is intended, for example, controller 40 may be configured to compare the changes in differential pressures between the pressures in first air blowing chamber 21*a* and the pressures in second air blowing chamber 21*b* at a plurality of points, to thus check the respiration state of the patient.

Although no limitation is intended, for example, controller 40 may be configured to determine that air leakage from mask 82 or the like occurs when an average value MP21 of the differential pressure between the pressure in first air blowing chamber 21*a* and the pressure in second air blowing chamber 21*b* is greater than a prescribed value Mth (the second reference value or a leakage determination value).

Therefore, in some examples, controller 40 may not include flow rate value converter 61 and may be configured such that exhalation timing determiner 62 determines the exhalation timing based on the differential pressure obtained by differential pressure sensor 41. In some other examples, controller 40 may not include flow rate value converter 61 and exhalation timing determiner 62, and may be configured such that pressure command generator 63 generates a pressure command value based on the differential pressure obtained by differential pressure sensor 41.

Controller 40 may be configured to be capable of implementing all of the above-described functions or may be configured to be capable of implementing one or some of the above-described functions. Although no limitation is intended, for example, controller 40 may include a computer processor executing a computer program configured to implement one, some, or all of the above-described functions.

Controller 40 may be configured to rotationally drive fan 32 based on the results sensed by various types of sensors in addition to the result sensed by differential pressure sensor 41.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:

1. A fluid control device comprising:
   a suction port;
   an exhaust port;
   a fan unit including a fan and a fan case in which the fan is housed;
   a controller to control driving of the fan;
   a case including:
      a first air blowing chamber in communication with outside through the suction port;
      a second air blowing chamber in which the fan unit is housed; and
      a communication path through which the first air blowing chamber and the second air blowing chamber are in communication with each other; and
   a differential pressure sensor to sense a differential pressure between a pressure inside the first air blowing chamber and a pressure inside the second air blowing chamber; wherein
   the fluid control device is configured such that, when the fan is driven, gas is fed from the suction port through the first air blowing chamber and into the second air blowing chamber, and the gas is suctioned from inside the second air blowing chamber into the fan unit.

2. The fluid control device according to claim 1, wherein
   the differential pressure sensor is configured to sense the differential pressure between the pressure inside the first air blowing chamber and the pressure inside the second air blowing chamber;
   the pressure inside the first air blowing chamber is obtained by a first pressure sensor to sense the pressure inside the first air blowing chamber; and
   the pressure inside the second air blowing chamber is obtained by a second pressure sensor to sense the pressure inside the second air blowing chamber.

3. The fluid control device according to claim 1, wherein the controller is configured or programmed to:
   control a rotation speed of the fan to be increased when the differential pressure is positive relative to a prescribed value; and
   control the rotation speed of the fan to be decreased when the differential pressure is negative relative to the prescribed value.

4. The fluid control device according to claim 1, wherein the controller is configured or programmed to:
   determine that a respiration state of a patient connected to the exhaust port is an inhalation state when the differential pressure is positive relative to a prescribed value; and
   determine that the respiration state of the patient connected to the exhaust port is an exhalation state when the differential pressure is negative relative to the prescribed value.

5. The fluid control device according to claim 1, wherein
   the case includes a control chamber in which the controller is housed, the control chamber being located adjacent to the first air blowing chamber and the second air blowing chamber;
   the first pressure sensing portion is defined by a first pressure sensing hole provided in a dividing wall between the first air blowing chamber and the control chamber, the first pressure sensing hole being opened toward the first air blowing chamber; and
   the second pressure sensing portion is defined by a second pressure sensing hole provided in a dividing wall between the second air blowing chamber and the control chamber, the second pressure sensing hole being opened toward the second air blowing chamber.

6. The fluid control device according to claim 5, wherein
   the first pressure sensing hole is opened in a direction orthogonal or substantially orthogonal to a direction in which the suction port is opened; and
   the second pressure sensing hole is opened in a direction orthogonal or substantially orthogonal to a direction in which the communication portion is opened.

7. The fluid control device according to claim 1, wherein the controller is configured or programmed to:
   convert the differential pressure into a flow rate of the fluid; and
   control the fan based on the flow rate.

8. The fluid control device according to claim 7, wherein the controller is configured or programmed to:
   estimate an exhalation timing based on the flow rate; and
   control the fan in accordance with the exhalation timing to change a pressure of the fluid.

9. The fluid control device according to claim 1, further comprising a pressure sensor provided in the fan case to detect pressure of gas discharged from the fan unit.

10. A continuous positive airway pressure device, comprising:
    the fluid control device according to claim 1;
    a mask; and
    a tube connecting the fluid control device to the mask.

11. The continuous positive airway pressure device according to claim 10, wherein
    the differential pressure sensor is configured to sense the differential pressure between the pressure inside the first air blowing chamber and the pressure inside the second air blowing chamber;
    the pressure inside the first air blowing chamber is obtained by a first pressure sensor to sense the pressure inside the first air blowing chamber; and
    the pressure inside the second air blowing chamber is obtained by a second pressure sensor to sense the pressure inside the second air blowing chamber.

12. The continuous positive airway pressure device according to claim 10, wherein the controller is configured or programmed to:
    control a rotation speed of the fan to be increased when the differential pressure is positive relative to a prescribed value; and
    control the rotation speed of the fan to be decreased when the differential pressure is negative relative to the prescribed value.

13. The continuous positive airway pressure device according to claim 10, wherein the controller is configured or programmed to:
    determine that a respiration state of a patient connected to the exhaust port is an inhalation state when the differential pressure is positive relative to a prescribed value; and determine that the respiration state of the patient connected to the exhaust port is an exhalation state when the differential pressure is negative relative to the prescribed value.

14. The continuous positive airway pressure device according to claim 10, wherein
the case includes a control chamber in which the controller is housed, the control chamber being located adjacent to the first air blowing chamber and the second air blowing chamber;
the first pressure sensing portion is defined by a first pressure sensing hole provided in a dividing wall between the first air blowing chamber and the control chamber, the first pressure sensing hole being opened toward the first air blowing chamber; and
the second pressure sensing portion is defined by a second pressure sensing hole provided in a dividing wall between the second air blowing chamber and the control chamber, the second pressure sensing hole being opened toward the second air blowing chamber.

15. The continuous positive airway pressure device according to claim 14, wherein
the first pressure sensing hole is opened in a direction orthogonal or substantially orthogonal to a direction in which the suction port is opened; and
the second pressure sensing hole is opened in a direction orthogonal or substantially orthogonal to a direction in which the communication portion is opened.

16. The continuous positive airway pressure device according to claim 10, wherein the controller is configured or programmed to:
convert the differential pressure into a flow rate of the fluid; and
control the fan based on the flow rate.

17. The continuous positive airway pressure device according to claim 16, wherein the controller is configured or programmed to:
estimate an exhalation timing based on the flow rate; and
control the fan in accordance with the exhalation timing to change a pressure of the fluid.

18. The continuous positive airway pressure device according to claim 10, further comprising a pressure sensor provided in the fan case to detect pressure of gas discharged from the fan unit.

* * * * *